(12) United States Patent
Kim (10) Patent No.: US 10,231,971 B2
(45) Date of Patent: Mar. 19, 2019

(54) PHARMACEUTICAL COMPOSITION FOR PREVENTING AND TREATING DRY EYE DISEASES, CONTAINING IMATINIB AS ACTIVE INGREDIENT

(71) Applicant: AVIXGEN INC., Seoul (KR)

(72) Inventor: Mi Jeong Kim, Yongin-si (KR)

(73) Assignee: AVIXGEN INC., Seoul (KR)

( * ) Notice: Subject to any disclaimer, the term of this patent is extended or adjusted under 35 U.S.C. 154(b) by 0 days.

(21) Appl. No.: 15/738,859

(22) PCT Filed: Jun. 22, 2016

(86) PCT No.: PCT/KR2016/006616
§ 371 (c)(1),
(2) Date: Dec. 21, 2017

(87) PCT Pub. No.: WO2016/208961
PCT Pub. Date: Dec. 29, 2016

(65) Prior Publication Data
US 2018/0193339 A1    Jul. 12, 2018

(30) Foreign Application Priority Data

Jun. 22, 2015 (KR) .................. 10-2015-0088701

(51) Int. Cl.
| | | |
|---|---|---|
| *A61K 31/501* | (2006.01) | |
| *A61K 31/506* | (2006.01) | |
| *A61K 9/00* | (2006.01) | |
| *A61K 31/496* | (2006.01) | |
| *A61K 31/497* | (2006.01) | |
| *A61P 27/04* | (2006.01) | |

(52) U.S. Cl.
CPC .............. *A61K 31/506* (2013.01); *A61K 9/00* (2013.01); *A61K 9/0048* (2013.01); *A61K 31/496* (2013.01); *A61K 31/497* (2013.01); *A61P 27/04* (2018.01)

(58) Field of Classification Search
CPC .................................................. A61K 31/506

USPC .................................................... 514/252.18
See application file for complete search history.

(56) References Cited

U.S. PATENT DOCUMENTS

| 2008/0119479 A1 | 5/2008 | Wedge | |
|---|---|---|---|
| 2009/0180986 A1 | 7/2009 | Schiffman | |
| 2009/0324718 A1* | 12/2009 | Zalit ...................... | A61K 9/146 424/474 |
| 2015/0079155 A1 | 3/2015 | Jensen et al. | |
| 2015/0224055 A1 | 8/2015 | Santos et al. | |

FOREIGN PATENT DOCUMENTS

| CN | 103083671 A | | 5/2013 |
|---|---|---|---|
| KR | 20070072543 A | | 7/2007 |
| KR | 20130141998 A | | 12/2013 |
| KR | 20150042215 A | | 4/2015 |
| KR | 20150051493 A | | 5/2015 |
| WO | WO2014074823 | * | 5/2015 |

OTHER PUBLICATIONS

International Search Report for International Application No. PCT/KR2016/006616 (3 Pages) (Oct. 21, 2016).
Vesaluoma et al., "Platelet-derived growth factor-BB (PDGF-BB) in tear fluid:a potential modulator of corneal wound healing following photorefractive keratectomy", Current Eye Research, 1997, pp. 825-831.

* cited by examiner

*Primary Examiner* — Rei Tsang Shiao
(74) *Attorney, Agent, or Firm* — Lucas & Mercanti, LLP (57) ABSTRACT

The present invention relates to a composition for preventing or treating dry eye syndrome or eye diseases caused by dry dyes, containing imatinib as an active ingredient and, more specifically, to an eye bath lotion for preventing or treating dry eye syndrome or eye diseases associated with dry eye syndrome, containing imatinib an active ingredient. Imatinib of the present invention effectively protects the corneal epithelia and inhibits the degeneration thereof, thereby being usable for a use of alleviating or treating dry eye syndrome or eye diseases associated with dry eye syndrome.

4 Claims, 6 Drawing Sheets

PHARMACEUTICAL COMPOSITION FOR PREVENTING AND TREATING DRY EYE DISEASES, CONTAINING IMATINIB AS ACTIVE INGREDIENT

CROSS-REFERENCE TO RELATED APPLICATIONS

This application is a 371 of PCT/KR2016/006616, filed on Jun. 22, 2016 which claims the benefit of Korean Patent Application No. 10-2015-0088701, filed Jun. 22, 2015 and the contents of each of which are incorporated herein by reference.

TECHNICAL FIELD

The present invention relates to a composition for the prevention and treatment of dry eye syndrome or ocular diseases due to eye dryness which includes imatinib as an active ingredient, and more particularly, to an eye drop for the prevention and treatment of dry eye syndrome or dry eye syndrome-associated ocular diseases which includes imatinib as an active ingredient.

BACKGROUND ART

Human eyes, which are responsible for vision, are vital sensory organs that accept most information needed for life. The eye consists of the cornea and conjunctiva on the anterior surface, the iris and ciliary body in the sclera surrounding the eye, the lens, the vitreous body to maintain a spherical shape of the eye, and the posterior retina. The lens, vitreous body, and aqueous humor correspond to a refractive medium. Visual impairment or blindness of the eyes due to diseases is one of the biggest factors that reduce the quality of life.

Dry eye syndrome, which is also referred to as dry eye or keratoconjunctivitis sicca, is a disease associated with dryness of the ocular surface, i.e., the cornea and conjunctiva, due to a lack of tears or excessive evaporation of tears and is known as a disorder of the tear film. According to the International Dry Eye Workshop (DEWS) and the National Eye Institute (NEI) of the United States, dry eye syndrome refers to eye discomfort, tear film instability, and tear and eye surface diseases that cause vision loss. Dryness of the ocular surface affects damage to and inflammation of the corneal epithelium which is protected by the tear film. When the amount of the tear film is insufficient due to an increase in evaporation of the tear film or low secretion of tears from the lacrimal gland, an osmolarity of the tear film and friction of the ocular surface increase due to the lack of tears, thus causing inflammation due to damage to the corneal epithelium. Dry eye syndrome may be classified into aqueous tear-deficient dry eye syndrome and evaporative dry eye syndrome. The aqueous tear-deficient dry eye syndrome is caused by the lack of tears secreted in lacrimal gland. The evaporative dry eye syndrome is caused by excessive moisture loss from the ocular surface due to the lack of a viscous substance in tears occurring as a result of a reduced secretory ability of goblet cells of the conjunctiva and Meibomian gland of the eyelid although lacrimal gland secretion normally functions. These causes are divided into intrinsic causes due to intrinsic diseases that affect an eyelid structure or dynamics, and extrinsic causes leading to fast destruction of the tear film of the ocular surface due to partial external exposure.

Factors that cause dry eye syndrome are highly diverse, and non-limiting examples of such factors may include reduced tear secretion, excessive tear evaporation, inflammation of tear-producing organs, a case in which systemic diseases such as Sjogren's syndrome or Stevens Johnson syndrome are involved, a long-term use of smartphones, tablet PCs, or the like, and a rapid change in hormone.

Artificial tears and other treatments to reduce subjective symptoms, such as chondroitin sulfate, glutathione, hyaluronic acid, fibronectin, and serum eye drop are currently used to treat dry eye syndrome. But effects thereof have not yet been sufficient. Thus, the development of effective therapeutic agents for the treatment of dry eye syndrome has been required.

Meanwhile, imatinib is well known as Gleevec, which is a leukemia treatment drug, is a chronic myelogenous leukemia (CML) therapeutic agent, and was developed by Novartis. Imatinib selectively inhibits the activity of a tyrosine kinase produced by the Philadelphia gene (cancer genes created by the chromosomal translocation of Bcr and Abl genes), which is a major cause of CML. In addition, imatinib is also known to be effective in gastrointestinal stromal tumor (GIST) associated with stomach cancer in addition to CML. However, effects of imatinib on treating or preventing dry eye syndrome or dry eye syndrome-associated diseases have not yet been found.

DISCLOSURE

Technical Problem

The inventors of the present invention discovered a novel use of imatinib for the treatment of dry eye syndrome and dry eye syndrome-associated ocular diseases, thus completing the present invention. Therefore, in order to suppress damage to the corneal epithelium and involved inflammation in a dried state of a surface of the eye due to the lack of a tear film, imatinib is used as an eye drop to treat dry eye syndrome.

Therefore, the inventors of the present invention developed a pharmaceutical composition for the prevention or treatment of dry eye syndrome or dry eye syndrome-associated ocular diseases which includes imatinib as an active ingredient, thus completing the present invention.

Thus, an object of the present invention is to provide a pharmaceutical composition for the prevention or treatment of dry eye syndrome or dry eye syndrome-associated ocular diseases which includes imatinib as an active ingredient.

Another object of the present invention is to provide an eye drop including imatinib as an active ingredient.

Another object of the present invention is provide a method of treating dry eye syndrome or dry eye syndrome-associated ocular diseases by administering an effective amount of imatinib to a subject in need thereof.

Another object of the present invention is to provide a use of imatinib for preparing a therapeutic agent for dry eye syndrome or dry eye syndrome-associated ocular diseases.

Technical Solution

According to an embodiment of the present invention, there is provided a pharmaceutical composition for the prevention and treatment of dry eye syndrome or dry eye syndrome-associated ocular diseases which includes imatinib as an active ingredient.

According to another embodiment of the present invention, there is provided an eye drop for the prevention and treatment of dry eye syndrome or dry eye syndrome-associated ocular diseases which includes imatinib as an active ingredient.

According to another embodiment of the present invention, there is provided a method of treating dry eye syndrome or dry eye syndrome-associated ocular diseases by administering an effective amount of imatinib to a subject in need thereof.

According to another embodiment of the present invention, there is provided a use of imatinib for preparing a therapeutic agent for dry eye syndrome or dry eye syndrome-associated ocular diseases.

Hereinafter, the present invention will be described in detail.

As used herein, the term "xerophthalmia," also known as dry eye or keratoconjunctivitis sicca, refers to ocular diseases including damage to a surface of the eye, sore eyes, and subjective symptoms such as irritation, a feeling of a foreign body, and dryness, due to a lack of tears, excessive tear evaporation, or an imbalance between constituents of tears.

The term "imatinib" as used herein is well known as Gleevec, which is a leukemia treatment drug, is a chronic myelogenous leukemia (CML) therapeutic agent, and was developed by Novartis. Imatinib selectively inhibits the activity of a tyrosine kinase produced by the Philadelphia gene (cancer genes created by the chromosomal translocation of Bcr and Abl genes), and is represented by Formula I below:

<Formula I>

The term "keratoconjunctivitis sicca" as used herein refers to inflammatory diseases occurring in the cornea and the conjunctiva due to bacteria, viruses, allergies, or environmental factors, and is the most generally occurring ocular diseases. Keratoconjunctivitis sicca is well cured in normal cases, but is fatal in some cases, thus causing blindness due to tissue damage. Keratoconjunctivitis sicca is largely classified into infectious conjunctivitis and non-infectious conjunctivitis.

The present invention provides a pharmaceutical composition for the prevention or treatment of dry eye syndrome or dry eye syndrome-associated ocular diseases which includes imatinib as an active ingredient.

In the present invention, examples of the dry eye syndrome-associated ocular diseases include keratoconjunctivitis sicca, corneal ulcer due to dryness, blepharitis (eyelid inflammation), eye redness, and corneal neovascularization.

In the present invention, the dry eye syndrome is an aqueous tear-deficient dry eye syndrome or evaporative dry eye syndrome.

As used herein, the term "aqueous tear-deficient dry eye syndrome" refers to dry eye syndrome having symptoms resulting from a dry ocular surface due to a lack of tears or one component of tears. As used herein, the term "evaporative dry eye syndrome" refers to a disease in which the tear film exhibit inadequate lubrication on a surface of the eye due to excessive evaporation of the tear film, and thus the surface of the eye becomes dry, resulting in discomfort and irritation symptoms.

In the present invention, the content of imatinib ranges from 0.005 wt % to 5 wt % based on a total weight of the composition. That is, the composition of the present invention may include a mixture of 0.005 wt % to 5 wt % of imatinib and 95 wt % to 99.995 wt % of a carrier.

The composition of the present invention is in the form of a suspension, powder, granules, tablets, sustained release preparations, injections, ointment, an eye drop, capsules, a contact lens cleaner, or a contact lens lubricant.

The preparation may include a pharmaceutically acceptable carrier, a diluent, an excipient, or a combination thereof according to need. These preparations facilitate administration of an active ingredient to the inside of an organism.

The carrier is defined as a compound that facilitates the addition of a compound into a cell or tissue. The carrier is not particularly limited as long as it is generally used according to formulation, but may be at least one selected from the group consisting of solid carriers such as starch, lactose, mannitol, carboxymethylcellulose, corn starch, an inorganic salt, and the like; liquid carriers such as distilled water, saline, an aqueous glucose solution, an alcohol such as ethanol or the like, propylene glycol, and polyethylene glycol; and oily carriers such as a variety of animal and plant oils, white petrolatum, paraffin, wax, and the like.

The excipient may be, for example, a filler such as lactose, sucrose, mannitol, or sorbitol, a cellulose-based substance such as corn starch, wheat starch, rice starch, potato starch, gelatin, gum tragacanth, methylcellulose, hydroxypropylmethyl-cellulose, sodium carboxymethylcellulose, and/or polyvinylpyrrolidone (PVP), or the like.

The pharmaceutical preparation may be formulated using a known method, and is preferably in the form of a pharmaceutically acceptable oral, external application, transdermal, or transmucosal preparation, including powder, granules, solutions, pills, troche, suspensions, emulsions, syrup, tablets, hard or soft capsules, injectable preparations, and unit dose type or multiple dose type preparations for parenteral administration. More preferably, the pharmaceutical preparation may be an oral preparation or an eye drop.

The present invention provides an eye drop for the prevention or treatment of dry eye syndrome or dry eye syndrome-associated ocular diseases which includes imatinib as an active ingredient.

The eye drop of the present invention may further include a thickener. The thickener of the present invention refers to a pharmaceutical or edible thickener generally used in the art, and non-limiting examples of the thickener include chitosan, hydroxypropylmethylcellulose (HPMC), hydroxypropylcellulose (HPC), hydroxyethylcellulose (HEC), polyvinylpyrrolidone (PVP), carboxymethylcellulose (CMC), carbomer, glycerin, polyethyleneoxide (PEO), and hyaluronic acid.

The eye drop of the present invention may further include an aqueous solution-containing carrier and is in a liquid form, and the aqueous solution-containing carrier may be at least one pharmaceutically acceptable carrier selected from the group consisting of distilled water, phosphate buffered saline, a balanced salt solution, and saline.

An eye drop composition of the present invention may also include a pharmaceutically acceptable carrier. As used herein, the term "pharmaceutically acceptable carrier" refers to a carrier or diluent that does not significantly stimulate an organism and does not inhibit the biological activity and properties of administered active ingredients. The pharmaceutically acceptable carrier may be, for example, an isotonic agent, a buffer, a stabilizer, a pH adjusting agent, a diluent, or the like. The diluent may include distilled water, phosphate buffered saline, a balanced salt solution, saline, a mixture thereof, or the like. In this regard, the amount of the diluent in the eye drop composition may be adjusted to that required to prepare a total amount of the active ingredient in the eye drop composition. In other words, the concentration of the active ingredient in the eye drop composition may be regulated by using the diluent.

The eye drop according to the present invention may be in the form of a liquid preparation. The eye drop of the present invention is used to treat dry eye syndrome or dry eye syndrome-associated ocular diseases.

The eye drop composition of the present invention may be used in the form of a mixture of imatinib as a main ingredient thereof and 0.05% to 0.5% of hyaluronic acid or CMC, more preferably, a mixture of imatinib and 0.1% of hyaluronic acid or CMC, or the mixture may be administered in combination with artificial tears, thereby maximizing a therapeutic effect in treating dry eye syndrome or dry eye syndrome-associated ocular diseases. In pharmaceutical perspectives, when the weight ratio is less than the above range, inadequate problems occur in wetting and lubricating action due to too low viscoelasticity, and, when the weight ratio is outside the above range, inadequate problems occur in permeability due to excessively high viscoelasticity, and thus it is difficult to secure appropriate fluidity as an eye drop.

The pharmaceutical composition or eye drop of the present invention is administered locally or administered dropwise to an eye.

As used herein, the term "administration" refers to introduction of the pharmaceutical composition of the present invention into a patient in any appropriate manner, and administration route of the composition of the present invention may include a variety of routes such as oral or parenteral administration route as long as it enables the composition to reach a target tissue. Preferably, the composition of the present invention is locally administered to an eye. The treatment method of the present invention includes administering imatinib in a pharmaceutically effective amount. It will be obvious to one of ordinary skill in the art that a suitable total daily dose may be determined by a practitioner within sound medical judgement. A specific therapeutically effective amount for a particular patient may vary depending on a variety of factors including the type and extent of response to be achieved, a specific composition as well as whether or not other preparations are used in some cases, age and body weight of a patient, normal health conditions, gender and diet, administration time, administration route, excretion rate of the composition, treatment period, a drug used in combination of the specific composition or concurrently used therewith, and similar factors well known in the medical field.

Although the present invention is primarily related to the treatment of a human, the present invention may target other mammals such as dogs, cats, and the like in need of the composition of the present invention, for veterinary purposes.

A dosage unit may include, for example, 1, 2, 3, or 4 times an individual dose or ½, ⅓, or ¼ times the individual dose. The individual dose preferably includes an amount of an active drug administered once (1 to 2 drops, 50 μl), and generally corresponds to a total of, ½, ⅓, or ¼ times a daily dose. An effective dose of imatinib is concentration-dependent, but ranges preferably from 0.005 wt % to 5 wt %, more preferably, from 0.01 wt % to 1 wt %, and may be administered once to six times a day.

Figure 2:
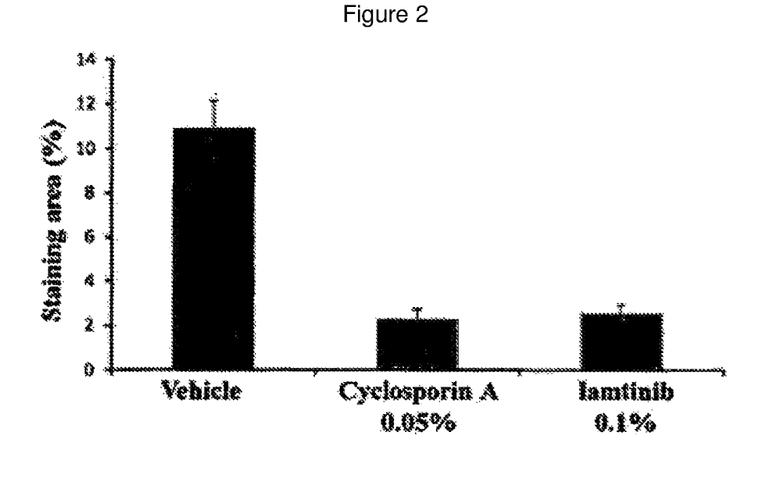
FIG. 2 is a graph showing a range of the lissamine green staining of FIG. 1, represented as values, to observe an effect of a drug in treating corneal damage.
Figure 3:
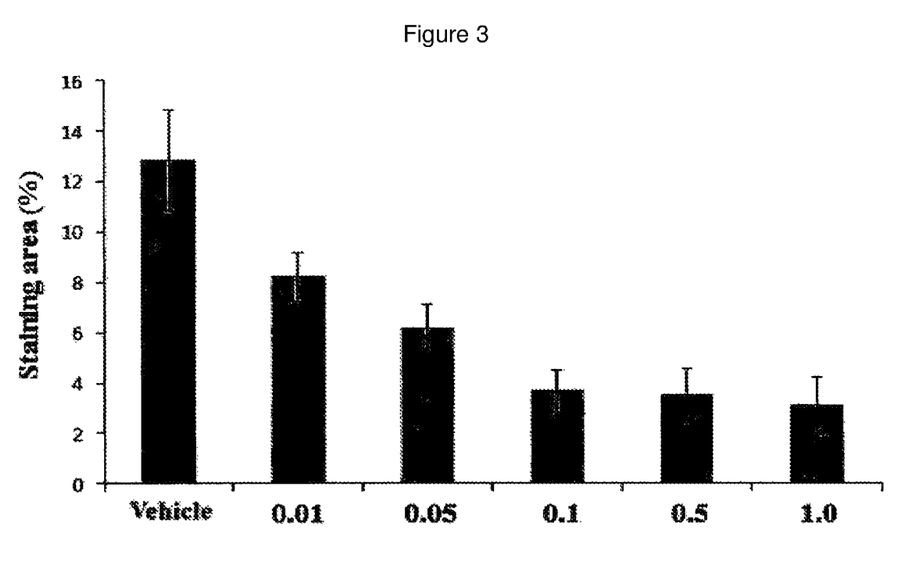
FIG. 3 is a graph showing a stained range of a keratoconjunctivitis sicca animal model that was administered imatinib according to concentration, and then stained with a 1% lissamine green dye solution to observe an effect of the drug, wherein the stained range is represented as values.

In Example 1 of the present invention, it was confirmed that, when a keratoconjunctivitis sicca model was treated with an imatinib eye drop, the imatinib eye drop had an effect of protecting the corneal epithelium. In this case, corneal damage was identified by staining a surface of the cornea with a 1% lissamine green solution and observing a damaged region thereof. As a result, it was confirmed that corneal damage was significantly inhibited in an imatinib-administered group and a Cyclosporin A-administered group, compared to a control (see FIG. 2). In addition, concentration-dependent effects thereof were confirmed (see FIG. 3).

Figure 4:
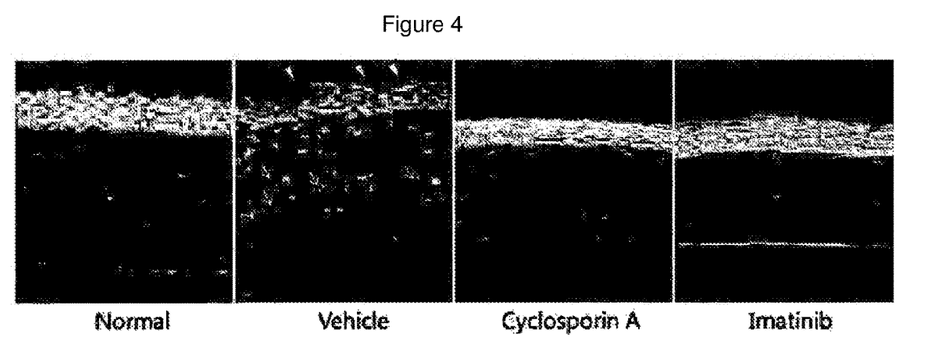
FIG. 4 is an image showing the corena of an imatinib eye drop-administered keratoconjunctivitis sicca animal model that was cryosectioned and stained with F-actin to observe a change in the corena.

In Example 2 of the present invention, it was confirmed that, when a keratoconjunctivitis sicca model was treated with an imatinib eye drop, the imatinib eye drop had a corneal degeneration protection effect. In this case, to observe corneal degeneration, F-actin staining was performed. As a result, corneal epithelial cells were keratinized in a control, while keratinization was not observed in the imatinib-treated group (see FIG. 4).

Figure 6:
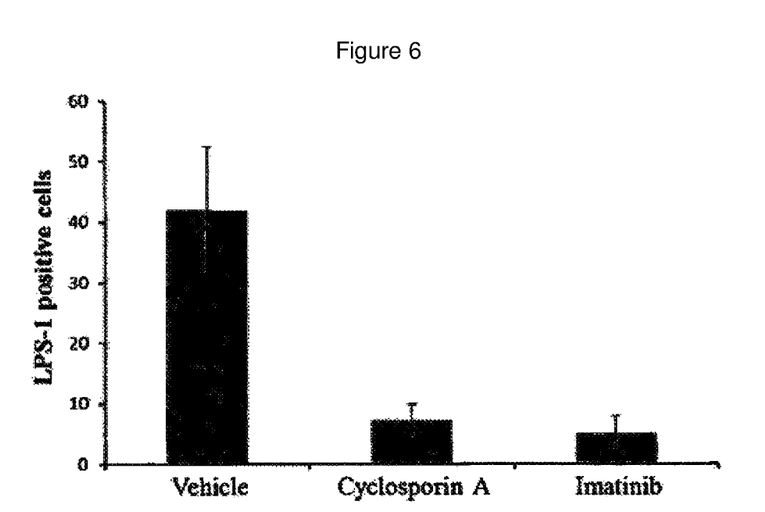
FIG. 6 is a graph showing the number of LPS-1-stained cells of tissue of the keratoconjunctivitis sicca animal model of FIG. 5, wherein the tissue was immunostained using an LPS-1 antibody.

In Example 3 of the present invention, an inflammation inhibitory effect of an imatinib eye drop on specific inflammatory cells was confirmed in a keratoconjunctivitis sicca model. Inflammatory cells having an antigen of LSP-1 were stained and observed, and, as a result, much fewer inflammatory cells than those in a control were observed (see FIG. 6).

As described in Examples above, a composition or eye drop including imatinib as an active ingredient has an effect of inhibiting corneal damage, corneal degeneration, and inflammation, and thus may effectively prevent and treat dry eye syndrome or dry eye syndrome-associated diseases.

The present invention provides a method of treating dry eye syndrome or dry eye syndrome-associated ocular diseases by administering an effective amount of imatinib to a subject in need thereof.

The present invention also provides a use of imatinib for preparing a therapeutic agent for dry eye syndrome or dry eye syndrome-associated ocular diseases.

The term "effective amount" as used herein refers to an amount sufficient to treat and prevent dry eye syndrome or dry eye syndrome-associated ocular diseases when administered to a patient. The term "subject" as used herein may include mammals, in particular, animals including humans, and cells, tissues, organs, and the like derived from animals. The subject may be a patient in need of treatment.

Advantageous Effects

Therefore, the present invention provides a pharmaceutical composition and eye drop for the alleviation or treatment of dry eye syndrome or dry eye syndrome-associated ocular diseases which include imatinib as an active ingredient. Imatinib of the present invention effectively protects the corneal epithelium and inhibits corneal degeneration, and thus may be usefully used to alleviate or treat dry eye syndrome or dry eye syndrome-associated ocular diseases.

MODE

Hereinafter, the present invention will be described in detail.

The following Examples are provided for illustrative purposes only, but are not intended to limit the scope of the present invention.

Example 1

Corneal Epithelium Protection Effect of Imatinib Eye Drop in Keratoconjunctivitis Sicca Model To carry out an experiment for dry corneal epithelial damage, a dry eye animal model was constructed. 8-week-old Sprague-Dawley (SD) rats (available from Orient Bio) were used as an animal, keratoconjunctivitis sicca was induced by administering an eye drop containing 0.1% benzalkonium chloride (Sigma Aldrich) in 1% atropine sulfate (Alcon) twice a day for 2 weeks.

The imatinib eye drop was prepared using a balanced salt solution, and had a pH of 6.8 to 7.4.

The imatinib eye drop (1 mg/ml) was administered dropwise to an eye twice a day for 1 week after 7 days of administration of 1% atropine sulfate and 0.1% benzalkonium chloride. To compare therapeutic effects, a 0.05% Cyclosporin eye drop (Restasis, Allergan) was used as a reference drug.

Figure 1:
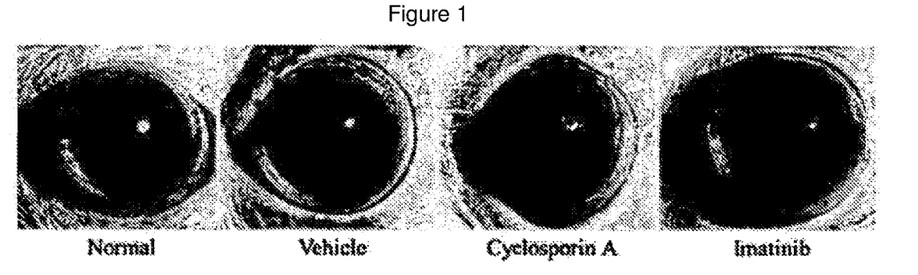
FIG. 1 is an image showing corneal damage (a region stained blue) of a keratoconjunctivitis sicca animal model administered each of imatinib (0.1%) and Cyclosporin A (0.05%) and then stained with a 1% lissamine green dye solution.

Corneal epithelial damage was identified in the keratoconjunctivitis sicca animal model by staining a surface of the cornea with a 1% lissamin green solution and observing a damaged region thereof (see FIG. 1).

Damage to corneal epithelium cells due to dryness was identified in a keratoconjunctivitis sicca (dry eye)-induced cornea by staining a dried state of the corneal epithelium cells with lissamin green (see FIG. 1). Lissamine green does not stain a normal cornea or the cornea having conjunctival epithelial cells, but a damaged corneal region or a corneal region not containing the corneal epithelium is stained blue with lissamine green. A stained area after staining was expressed as a percentage (%) with respect to a total corneal area. It was confirmed that a surface of the cornea was stained by 11±1.26% in a control (vehicle, a drug-non-treated group), while lissamine green staining of the surface of the cornea was significantly reduced to 2.3±0.43% in Cyclosporin A (0.05%) and to 2.6±0.39% in imatinib (0.1%) (See FIG. 2). In addition, it was confirmed that, when administered imatinib according to concentration, the animal model exhibited a concentration-dependent effect (See FIG. 3). In the concentration-dependent efficacy test, the surface of the cornea was stained by 12.8±1.98% in a control (vehicle, a drug-non-treated group), while lissamine green staining of the surface of the cornea was significantly reduced to 8.2±0.97% in a 0.01% imatinib-administered group (0.1 mg/ml), 6.18±0.9% in a 0.05% imatinib-administered group (0.5 mg/ml), 3.7±0.87% in a 0.1% imatinib-administered group (1 mg/ml), 3.5±1.1% in a 0.5% imitanib-administered group (5 mg/ml), and 3.1±1.2% in a 1.0% imatinib-administered group (10 mg/ml).

Example 2

Corneal Degeneration Protection Effect of Imatinib Eye Drop in Keratoconjunctivitis Sicca Model An experiment for keratoconjunctivitis sicca was carried out using the same dry eye animal model as that constructed in Example 1. White SD rats were used as an animal, and keratoconjunctivitis sicca was induced by administering 1% atropine sulfate and 0.1% benzalkonium chloride dropwise to an eye twice a day for 2 weeks.

An imatinib eye drop (0.1 mg/ml) was administered dropwise to an eye twice a day for 1 week after 7 days of administration of 1% atropine sulfate and 0.1% benzalkonium chloride. A 0.05% Cyclosporin A eye drop was used as a reference drug.

In order to observe corneal degeneration in the keratoconjunctivitis sicca (dry eye) model, F-actin staining was performed. F-actin was stained with phalloidin labeled with a fluorescent material. Keratinization of corneal epithelial cells was observed in a vehicle not administered a drug (white arrow head), while cells stained in a tube form (white arrow) was observed in the corneal stroma. However, corneal degeneration observed in the vehicle was not observed in a vehicle administered each of Cyclosporin A and imatinib, and had no difference from a normal case (See FIG. 4).

Example 3

Effect of Imatinib Eye Drop in Inhibiting Invasion of Specific Inflammatory Cells in Keratoconjunctivitis Sicca An experiment was carried out using the same administration method as that used in the animal model of Example 1, and then an inflammation inhibitory effect of imatinib on specific inflammatory cells invaded into the cornea was identified.

Figure 5:
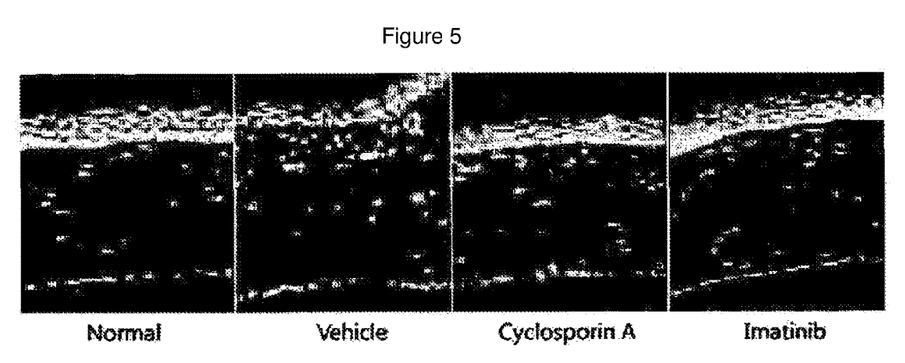
FIG. 5 is an image showing tissue of a cryosectioned cornea of an imatinib eye drop-administered keratoconjunctivitis sicca animal model, wherein the tissue was immunostained using an LPS-1 antibody to observe inflammatory cells in the corena.

To identify inflammatory cells in the cornea in keratoconjunctivitis sicca (dry eye), the eye was cryosectioned, and inflammatory cells having an antigen of LSP-1 were stained and observed (See FIG. 5). Inflammation-associated cells such as lymphocytes, neutrophils, and macrophages have LSP-1 can be observed after being immunostained using an LSP-1 antibody. Inflammatory cells were observed by 0.61±0.05 in a control (a drug-non-treated group) and by 0.52±0.05 in an imatinib eye drop (0.1%) (See FIG. 6). As a result of the inflammatory cell staining experiment, it was confirmed that the imatinib eye drop (0.1%) had an inflammation inhibitory effect on keratoconjunctivitis sicca.

In view of the above results, the imatinib eye drop of the present invention may be effectively used in treating keratoconjunctivitis sicca and inflammation of keratoconjunctivitis sicca due to eye dryness.

INDUSTRIAL APPLICABILITY

As is apparent from the foregoing description, the present invention provides a pharmaceutical composition and eye drop for the alleviation or treatment of dry eye syndrome or dry eye syndrome-associated ocular diseases which includes imatinib as an active ingredient. Imatinib of the present invention effectively protects the corneal epithelium and inhibits corneal degeneration, and thus may be usefully used in alleviating or treating dry eye syndrome or dry eye syndrome-associated ocular diseases, thus being industrially applicable.

The invention claimed is:

1. A method of treating dry eye syndrome or dry eye syndrome-associated ocular diseases, the method comprising administering an effective amount of a pharmaceutical composition to a subject in need thereof wherein the pharmaceutical composition comprises
imatinib as an active ingredient, and
an aqueous solution-containing carrier,
wherein the pharmaceutical composition is an eye drop in liquid form,
wherein the pharmaceutical composition is administered locally or administered dropwise to an eye, and
wherein dry eye syndrome-associated ocular diseases are selected from the group consisting of keratoconjunctivitis sicca, corneal ulcer due to dryness, blepharitis (eyelid inflammation) and eye redness.

2. The method of treating dry eye syndrome or dry eye syndrome-associated ocular diseases of claim 1, wherein the dry eye syndrome is aqueous tear-deficient dry eye syndrome or evaporative dry eye syndrome.

3. The method of treating dry eye syndrome or dry eye syndrome-associated ocular diseases of claim 1, wherein the pharmaceutical composition inhibits corneal degeneration and reduces the number of inflammatory cells.

4. The method of treating dry eye syndrome or dry eye syndrome-associated ocular diseases of claim 1, wherein a content of the imatinib ranges from 0.005 wt % to 5 wt % based on a total weight of the pharmaceutical composition.

* * * * *